United States Patent
Schimpf et al.

(10) Patent No.: US 9,492,599 B2
(45) Date of Patent: Nov. 15, 2016

(54) HALL SENSOR MOUNTING IN AN IMPLANTABLE BLOOD PUMP

(71) Applicant: Thoratec Corporation, Pleasanton, CA (US)

(72) Inventors: Samuel Schimpf, Weisslingen (CH); Mark McChrystal, San Ramon, CA (US); Joseph C. Stark, III, San Leandro, CA (US); Andre Siebenhaar, Gipf-Oberfrick (CH)

(73) Assignee: THORATEC CORPORATION, Pleasanton, CA (US)

( * ) Notice: Subject to any disclaimer, the term of this patent is extended or adjusted under 35 U.S.C. 154(b) by 128 days.

(21) Appl. No.: 14/015,542

(22) Filed: Aug. 30, 2013

(65) Prior Publication Data

US 2014/0067056 A1    Mar. 6, 2014

Related U.S. Application Data

(60) Provisional application No. 61/695,624, filed on Aug. 31, 2012.

(51) Int. Cl.
*A61M 1/10* (2006.01)
*A61M 1/12* (2006.01)
(Continued)

(52) U.S. Cl.
CPC .............. *A61M 1/12* (2013.01); *A61M 1/1086* (2013.01); *A61M 1/122* (2014.02); *F04D 13/064* (2013.01);
(Continued)

(58) Field of Classification Search
CPC .................. A61M 1/10; A61M 1/1031; A61M 1/122; A61M 1/12; G01B 7/003; H05K 1/028; H05K 3/30
(Continued)

(56) References Cited

U.S. PATENT DOCUMENTS

| 845,816 A | 3/1907 | Prindle |
| 888,654 A | 5/1908 | Prindle |

(Continued)

FOREIGN PATENT DOCUMENTS

| CN | 300837668D | 10/2008 |
| EP | 150320 B1 | 5/1990 |

(Continued)

OTHER PUBLICATIONS

Barletta and Schob, "Design of a bearingless blood pump" in Proc.3rd Int. Symp. on Magnetic Suspension Technology, Tallahassee FL, Dec. 13-15, 1995, pp. 265-274.
(Continued)

*Primary Examiner* — Theodore Stigell
*Assistant Examiner* — Michael Carey
(74) *Attorney, Agent, or Firm* — Kilpatrick Townsend & Stockton LLP

(57) ABSTRACT

A molded interconnect device can carry a Hall sensor for transducing a position of a rotor of the implantable blood pump. The molded interconnect device includes one or more integrated electronic circuit traces configured to electrically connect the hall sensor with a printed circuit board of the implantable blood pump, and the molded interconnect device is configured to be mounted to the printed circuit board.

18 Claims, 10 Drawing Sheets

(51) Int. Cl.
  *G01B 7/00* (2006.01)
  *H05K 1/02* (2006.01)
  *H05K 3/30* (2006.01)
  *F04D 13/06* (2006.01)
  *G01B 7/30* (2006.01)
  *H05K 1/11* (2006.01)
  *H05K 1/18* (2006.01)
  *F04D 15/00* (2006.01)
  *H05K 3/46* (2006.01)

(52) U.S. Cl.
  CPC ............ *F04D 15/0077* (2013.01); *G01B 7/003* (2013.01); *G01B 7/30* (2013.01); *H05K 1/028* (2013.01); *H05K 1/119* (2013.01); *H05K 1/189* (2013.01); *H05K 3/30* (2013.01); *A61M 1/1031* (2014.02); *H05K 3/4691* (2013.01); *H05K 2201/052* (2013.01); *H05K 2201/10151* (2013.01); *Y10T 29/49009* (2015.01); *Y10T 29/49128* (2015.01)

(58) Field of Classification Search
  USPC .................................. 600/16; 623/3.13, 3.14
  See application file for complete search history.

(56) References Cited

U.S. PATENT DOCUMENTS

| | | | |
|---|---|---|---|
| 1,026,101 | A | 5/1912 | Marsh |
| 2,128,988 | A | 9/1938 | Russell |
| 2,747,512 | A | 5/1956 | Paul |
| 2,864,552 | A | 12/1958 | Norman |
| 3,005,117 | A | 10/1961 | Buchhold |
| 3,066,849 | A | 12/1962 | Beams |
| 3,122,101 | A | 2/1964 | Baker et al. |
| 3,225,608 | A | 12/1965 | Ivan |
| 3,401,640 | A | 9/1968 | John et al. |
| 3,499,274 | A | 3/1970 | Fergason |
| 3,575,536 | A | 4/1971 | Jacobs et al. |
| 3,597,022 | A | 8/1971 | Waldron |
| 3,608,088 | A | 9/1971 | Dorman et al. |
| 3,611,815 | A | 10/1971 | Fischell |
| 3,647,324 | A | 3/1972 | Rafferty et al. |
| 3,650,581 | A | 3/1972 | Boden et al. |
| 3,938,913 | A | 2/1976 | Isenberg et al. |
| 3,957,389 | A | 5/1976 | Rafferty et al. |
| 4,082,376 | A | 4/1978 | Wehde et al. |
| 4,135,253 | A | 1/1979 | Reich et al. |
| 4,167,296 | A | 9/1979 | Dendy |
| 4,213,207 | A | 7/1980 | Wilson |
| 4,340,260 | A | 7/1982 | Forster et al. |
| 4,382,199 | A | 5/1983 | Isaacson |
| 4,398,773 | A | 8/1983 | Boden et al. |
| 4,405,286 | A | 9/1983 | Studer |
| 4,408,966 | A | 10/1983 | Maruyama |
| 4,475,866 | A | 10/1984 | Kambe et al. |
| 4,507,048 | A | 3/1985 | Belenger et al. |
| 4,547,039 | A | 10/1985 | Caron et al. |
| 4,589,822 | A | 5/1986 | Clausen et al. |
| 4,642,036 | A | 2/1987 | Young |
| 4,688,998 | A | 8/1987 | Olsen et al. |
| 4,704,121 | A | 11/1987 | Moise |
| 4,763,032 | A | 8/1988 | Bramm et al. |
| 4,779,614 | A | 10/1988 | Moise |
| 4,844,707 | A | 7/1989 | Kletschka |
| 4,876,492 | A | 10/1989 | Lester et al. |
| 4,878,831 | A | 11/1989 | Ewing |
| 4,898,759 | A | 2/1990 | Hoover et al. |
| 4,922,199 | A * | 5/1990 | Fukui .................. G01D 5/20 29/831 |
| 4,929,158 | A | 5/1990 | Girault |
| 4,944,748 | A | 7/1990 | Bramm et al. |
| 4,957,504 | A | 9/1990 | Chardack |
| 5,055,005 | A | 10/1991 | Kletschka |
| 5,078,741 | A | 1/1992 | Bramm et al. |
| 5,106,273 | A | 4/1992 | Lemarquand et al. |
| 5,112,200 | A | 5/1992 | Isaacson et al. |
| 5,112,202 | A | 5/1992 | Oshima et al. |
| 5,126,612 | A | 6/1992 | Girault |
| 5,127,792 | A | 7/1992 | Katsuta et al. |
| 5,159,219 | A | 10/1992 | Chu et al. |
| 5,177,387 | A | 1/1993 | McMichael et al. |
| 5,195,877 | A | 3/1993 | Kletschka |
| 5,220,232 | A | 6/1993 | Rigney et al. |
| 5,341,059 | A | 8/1994 | Fukuyama et al. |
| 5,385,581 | A | 1/1995 | Bramm et al. |
| 5,470,208 | A | 11/1995 | Kletschka |
| 5,652,473 | A | 7/1997 | Delamare et al. |
| 5,708,346 | A | 1/1998 | Schob |
| 5,725,357 | A | 3/1998 | Nakazeki et al. |
| 5,798,454 | A | 8/1998 | Nakazeki et al. |
| 5,808,437 | A | 9/1998 | Schob |
| 5,917,297 | A | 6/1999 | Gerster et al. |
| 5,928,131 | A | 7/1999 | Prem |
| 5,947,703 | A | 9/1999 | Nojiri et al. |
| 6,023,115 | A | 2/2000 | Maejima |
| 6,053,705 | A | 4/2000 | Schob et al. |
| 6,100,618 | A | 8/2000 | Schoeb et al. |
| 6,121,704 | A | 9/2000 | Fukuyama et al. |
| 6,130,494 | A | 10/2000 | Schob |
| 6,146,325 | A | 11/2000 | Lewis et al. |
| 6,191,513 | B1 | 2/2001 | Chen et al. |
| 6,222,290 | B1 | 4/2001 | Schöb et al. |
| 6,227,797 | B1 | 5/2001 | Watterson et al. |
| 6,232,687 | B1 | 5/2001 | Hollenbeck et al. |
| 6,234,772 | B1 | 5/2001 | Wampler et al. |
| 6,249,067 | B1 | 6/2001 | Schob et al. |
| 6,259,179 | B1 | 7/2001 | Fukuyama et al. |
| 6,264,635 | B1 | 7/2001 | Wampler et al. |
| 6,278,251 | B1 | 8/2001 | Schöb |
| 6,293,901 | B1 | 9/2001 | Prem |
| 6,302,661 | B1 | 10/2001 | Khanwilkar et al. |
| 6,348,752 | B1 | 2/2002 | Erdman et al. |
| 6,351,048 | B1 | 2/2002 | Schob et al. |
| 6,355,998 | B1 | 3/2002 | Schöb et al. |
| 6,394,769 | B1 | 5/2002 | Bearnson et al. |
| 6,447,266 | B2 | 9/2002 | Antaki et al. |
| 6,468,041 | B2 | 10/2002 | Ozaki |
| 6,559,567 | B2 | 5/2003 | Schöb |
| 6,575,717 | B2 | 6/2003 | Ozaki et al. |
| 6,589,030 | B2 | 7/2003 | Ozaki |
| 6,605,032 | B2 | 8/2003 | Benkowski et al. |
| 6,623,475 | B1 | 9/2003 | Siess |
| 6,626,644 | B2 | 9/2003 | Ozaki |
| 6,634,224 | B1 | 10/2003 | Schöb et al. |
| 6,640,617 | B2 | 11/2003 | Schöb et al. |
| 6,688,861 | B2 | 2/2004 | Wampler |
| 6,707,200 | B2 | 3/2004 | Carroll et al. |
| 6,711,943 | B1 | 3/2004 | Schöb |
| 6,717,311 | B2 | 4/2004 | Locke |
| 6,817,836 | B2 | 11/2004 | Nose et al. |
| 6,879,074 | B2 | 4/2005 | Amrhein et al. |
| 6,949,066 | B2 | 9/2005 | Bearnson et al. |
| 7,070,398 | B2 | 7/2006 | Olsen et al. |
| 7,112,903 | B1 | 9/2006 | Schob |
| 7,138,776 | B1 | 11/2006 | Gauthier et al. |
| 7,150,711 | B2 | 12/2006 | Nüsser et al. |
| D534,548 | S | 1/2007 | Urano et al. |
| 7,160,242 | B2 | 1/2007 | Yanai |
| 7,229,258 | B2 | 6/2007 | Wood et al. |
| 7,229,474 | B2 | 6/2007 | Hoffmann et al. |
| 7,239,098 | B2 | 7/2007 | Masino |
| 7,284,956 | B2 | 10/2007 | Nose et al. |
| 7,338,521 | B2 | 3/2008 | Antaki et al. |
| 7,462,019 | B1 | 12/2008 | Allarie et al. |
| 7,497,116 | B2 | 3/2009 | Miyakoshi et al. |
| 7,511,443 | B2 | 3/2009 | Townsend et al. |
| 7,578,782 | B2 | 8/2009 | Miles et al. |
| 7,591,777 | B2 | 9/2009 | Larose |
| 7,645,225 | B2 | 1/2010 | Medvedev et al. |
| 7,699,588 | B2 | 4/2010 | Mendler |
| 7,854,631 | B2 | 12/2010 | Townsendl et al. |
| 7,861,582 | B2 | 1/2011 | Miyakoshi et al. |
| 7,887,479 | B2 | 2/2011 | Larose et al. |

(56) References Cited

U.S. PATENT DOCUMENTS

| | | |
|---|---|---|
| 7,951,062 B2 | 5/2011 | Morello |
| 7,963,705 B2 | 6/2011 | Staeber et al. |
| 7,976,271 B2 | 7/2011 | LaRose et al. |
| 8,152,493 B2 | 4/2012 | LaRose et al. |
| 8,157,720 B2 | 4/2012 | Marseille et al. |
| 8,303,482 B2 | 11/2012 | Schima et al. |
| 8,382,830 B2 | 2/2013 | Maher et al. |
| 8,506,470 B2 | 8/2013 | Larose et al. |
| 8,517,699 B2 | 8/2013 | Horvath |
| 8,556,795 B2 | 10/2013 | Bolyard et al. |
| 8,597,350 B2 | 12/2013 | Rudser et al. |
| 8,764,621 B2 | 7/2014 | Badstibner et al. |
| 8,870,739 B2 | 10/2014 | Larose et al. |
| 8,882,477 B2 | 11/2014 | Fritz, IV et al. |
| 8,956,275 B2 | 2/2015 | Bolyard et al. |
| 8,981,245 B2 | 3/2015 | Dinh et al. |
| 2004/0236420 A1 | 11/2004 | Yamane et al. |
| 2005/0004421 A1 | 1/2005 | Pacella et al. |
| 2005/0147512 A1 | 7/2005 | Chen et al. |
| 2007/0100196 A1 | 5/2007 | LaRose et al. |
| 2008/0068815 A1 | 3/2008 | Astley et al. |
| 2009/0064755 A1 | 3/2009 | Fleischli et al. |
| 2009/0234447 A1 | 9/2009 | LaRose et al. |
| 2010/0130809 A1 | 5/2010 | Morello |
| 2010/0150749 A1 | 6/2010 | Horvath |
| 2010/0152526 A1 | 6/2010 | Pacella et al. |
| 2010/0241223 A1 | 9/2010 | Lee et al. |
| 2010/0327687 A1 | 12/2010 | Iannello et al. |
| 2011/0002794 A1 | 1/2011 | Haefliger et al. |
| 2011/0031836 A1 | 2/2011 | Nussbaumer |
| 2011/0054239 A1 | 3/2011 | Sutton et al. |
| 2011/0071337 A1 | 3/2011 | Thompson et al. |
| 2011/0144413 A1 | 6/2011 | Foster |
| 2011/0156197 A1 | 6/2011 | Tivarus et al. |
| 2011/0187217 A1 | 8/2011 | Nussbaumer |
| 2011/0237863 A1 | 9/2011 | Ricci et al. |
| 2011/0245582 A1 | 10/2011 | Zafirelis et al. |
| 2011/0313237 A1 | 12/2011 | Miyakoshi et al. |
| 2012/0032629 A1 | 2/2012 | Peterson et al. |
| 2012/0035411 A1 | 2/2012 | LaRose et al. |
| 2012/0046514 A1 | 2/2012 | Bourque |
| 2012/0059212 A1 | 3/2012 | LaRose et al. |
| 2012/0112347 A1 | 5/2012 | Eckhardt et al. |
| 2012/0126795 A1* | 5/2012 | Genoud ............ F04B 7/06 324/207.2 |
| 2012/0134832 A1 | 5/2012 | Wu |
| 2012/0226097 A1 | 9/2012 | Smith et al. |
| 2012/0245680 A1* | 9/2012 | Masuzawa ........ A61M 1/101 623/3.11 |
| 2012/0245681 A1 | 9/2012 | Casas et al. |
| 2012/0253103 A1 | 10/2012 | Robert |
| 2012/0310036 A1 | 12/2012 | Peters et al. |
| 2013/0164161 A1 | 6/2013 | Schob |
| 2013/0331934 A1 | 12/2013 | Kabir et al. |
| 2014/0062462 A1 | 3/2014 | McChrystal et al. |
| 2014/0100413 A1 | 4/2014 | Casas et al. |
| 2014/0194985 A1 | 7/2014 | Vadala, Jr. |
| 2014/0275723 A1 | 9/2014 | Fritz, IV et al. |
| 2014/0303426 A1 | 10/2014 | Kerkhoffs et al. |
| 2014/0357937 A1 | 12/2014 | Reyes et al. |
| 2015/0051438 A1 | 2/2015 | Taskin |

FOREIGN PATENT DOCUMENTS

| | | |
|---|---|---|
| EP | 378251 A2 | 7/1990 |
| EP | 60569 B1 | 12/1990 |
| EP | 2357374 A1 | 8/2011 |
| GB | 1491710 A | 11/1977 |
| JP | 1257792 A | 10/1989 |
| JP | 2016390 U | 2/1990 |
| JP | D1373017 | 10/2009 |
| TW | D136032 S1 | 7/2010 |
| WO | WO9953974 A2 | 10/1999 |
| WO | WO2010036815 A3 | 6/2010 |
| WO | WO2012028181 A1 | 3/2012 |
| WO | WO 2014/036419 A1 | 3/2014 |

OTHER PUBLICATIONS

Office Action for U.S. Appl. No. 13/212,813, dated Mar. 25, 2013, 6 pages.

Office Action for U.S. Appl. No. 13/212,813, dated Sep. 23, 2013, 9 pages.

International Preliminary Report on Patentability for Application No. PCT/US2011/048259, mailed Mar. 7, 2013, 9 pages.

International Search Report and Written Opinion for Application No. PCT/US2011/048259 mailed Dec. 20, 2011, 13 pages.

"IPC-4202 Flexible Base Dielectrics for Use in Flexible Printed Circuitry," Institute for Interconnecting and Packaging Electronic Circuits, reprinted from http://www.dynamixtechnology.com/docs/ipc-4202s.pdf, May 2002.

"IPC-4101 Reference Guide," reprinted from http://www.lyncolec.co.uk/page43.html (accessed 8-28-28).

"IPC-4101 Specification for Base Materials for Rigid and Multilayer Printed Boards," Institute for Interconnecting and Packaging Electronic Circuits, reprinted from http://www.hitech.com.mk/Resources/Documents/IPC-4101-MultiLayer-PCb-Materials.pdf, Dec. 1997.

"Flexible Circuits for Medical Device Manufacturers," AllFlex Inc., reprinted from http://www.allflexinc.com/medical-device.shtml (accessed Aug. 22, 2013).

"Rigid Flex Printed Circuit Boards," San Francisco Circuits, reprinted from http://www.sfcircuits.com/pcb-production-capabilities/rigid-flex-pcbs (accessed Aug. 22, 2013).

"Flexible Printed Circuit Boards, Flexible PCBs and Rigid Flex Circuits," Rigid-Flex Inc., reprinted from http://www.rigid-flex.com/ (accessed Aug. 22, 2013).

"Why Rigid Flex?," Printed Circuits Inc., reprinted from http://printedcircuits.com/ (accessed Aug. 22, 2013).

Notification of Transmittal of the International Search Report and the Written Opinion of the International Searching Authority, or the Declaration; International Search Report and Written Opinion of the International Searching Authority for corresponding International application No. PCT/US2013/057553 mailed on Dec. 13, 2013, 14 pages.

* cited by examiner

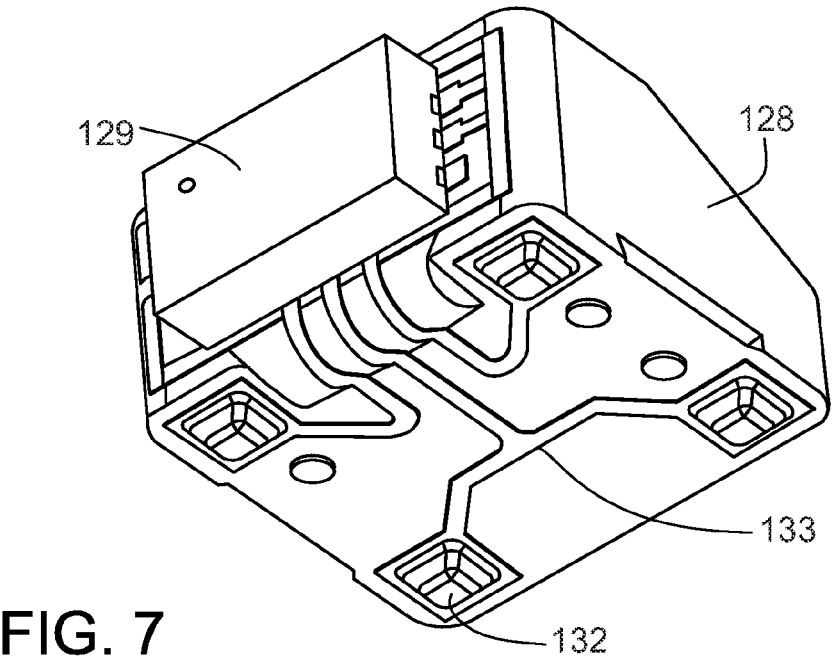
FIG. 7
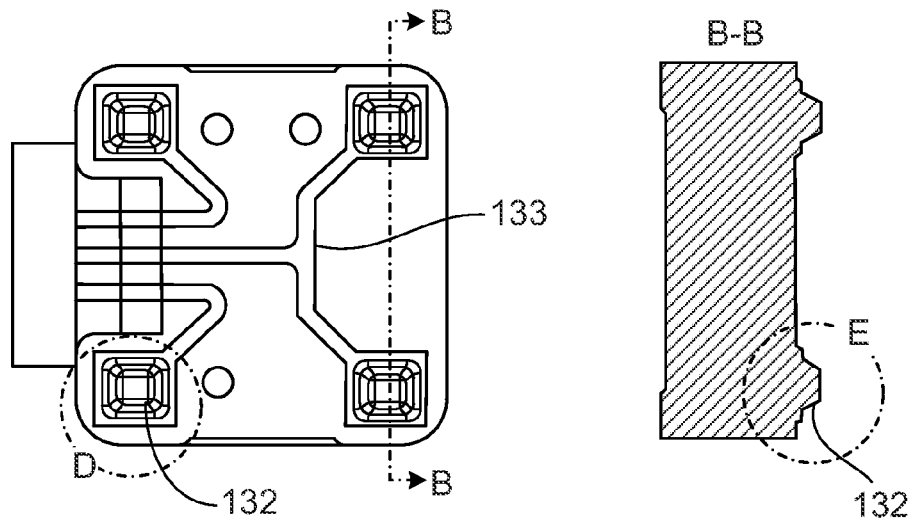
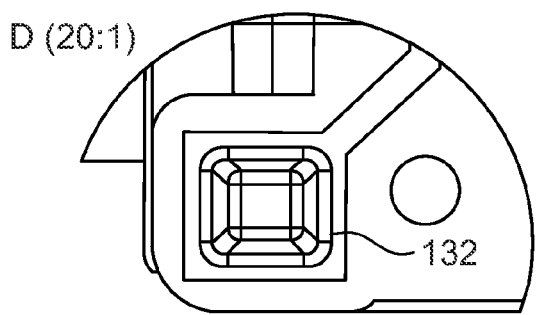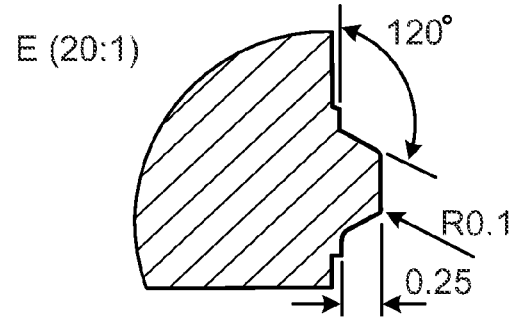

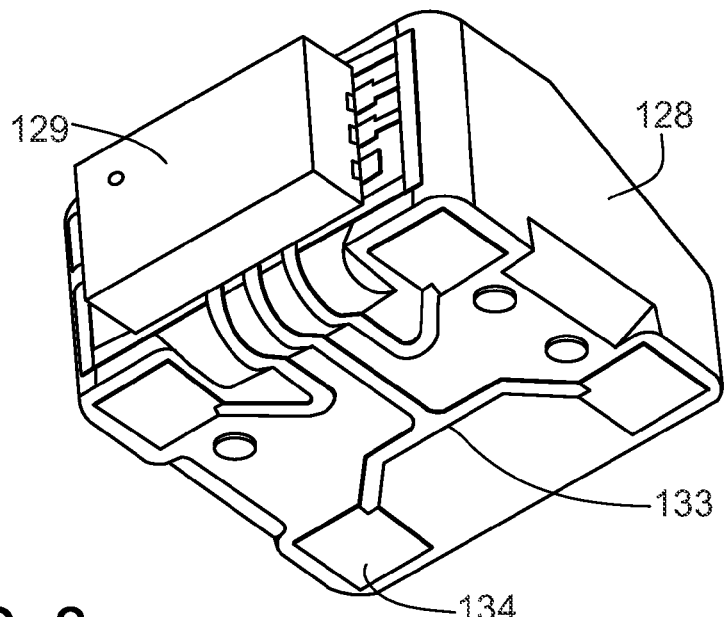
FIG. 8
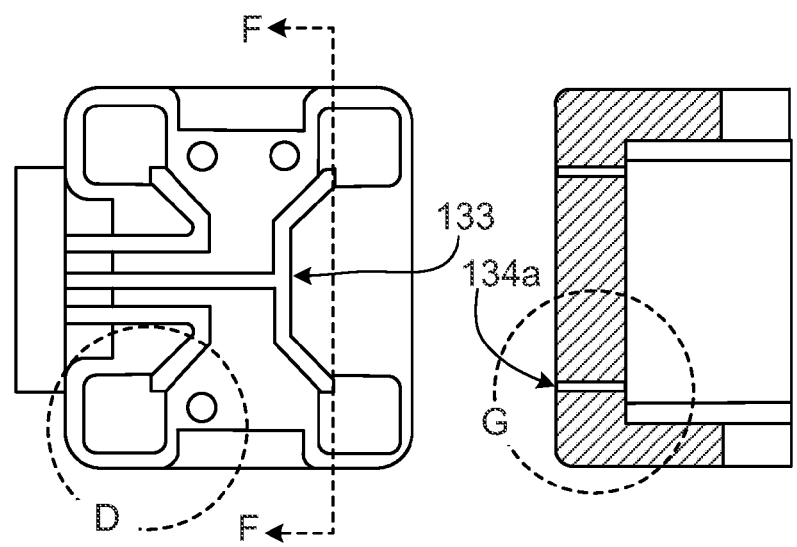
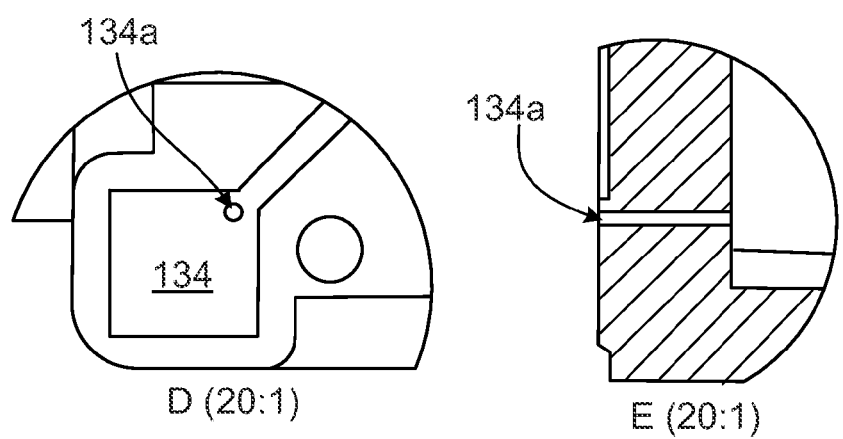

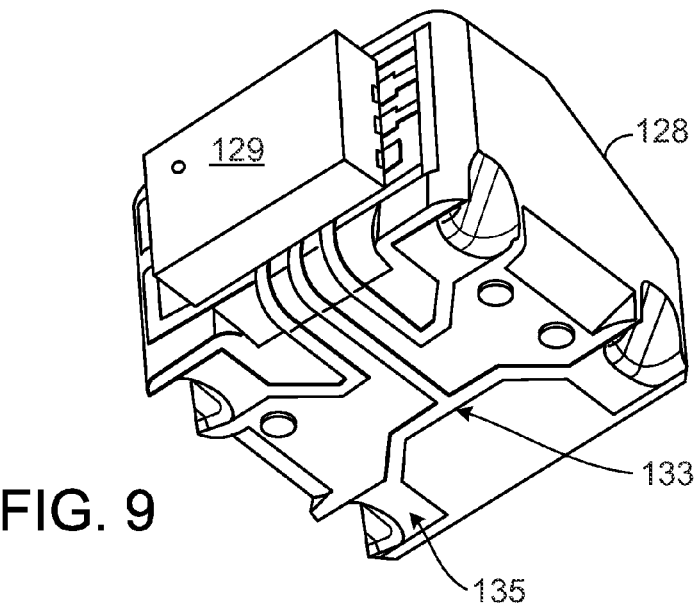
FIG. 9
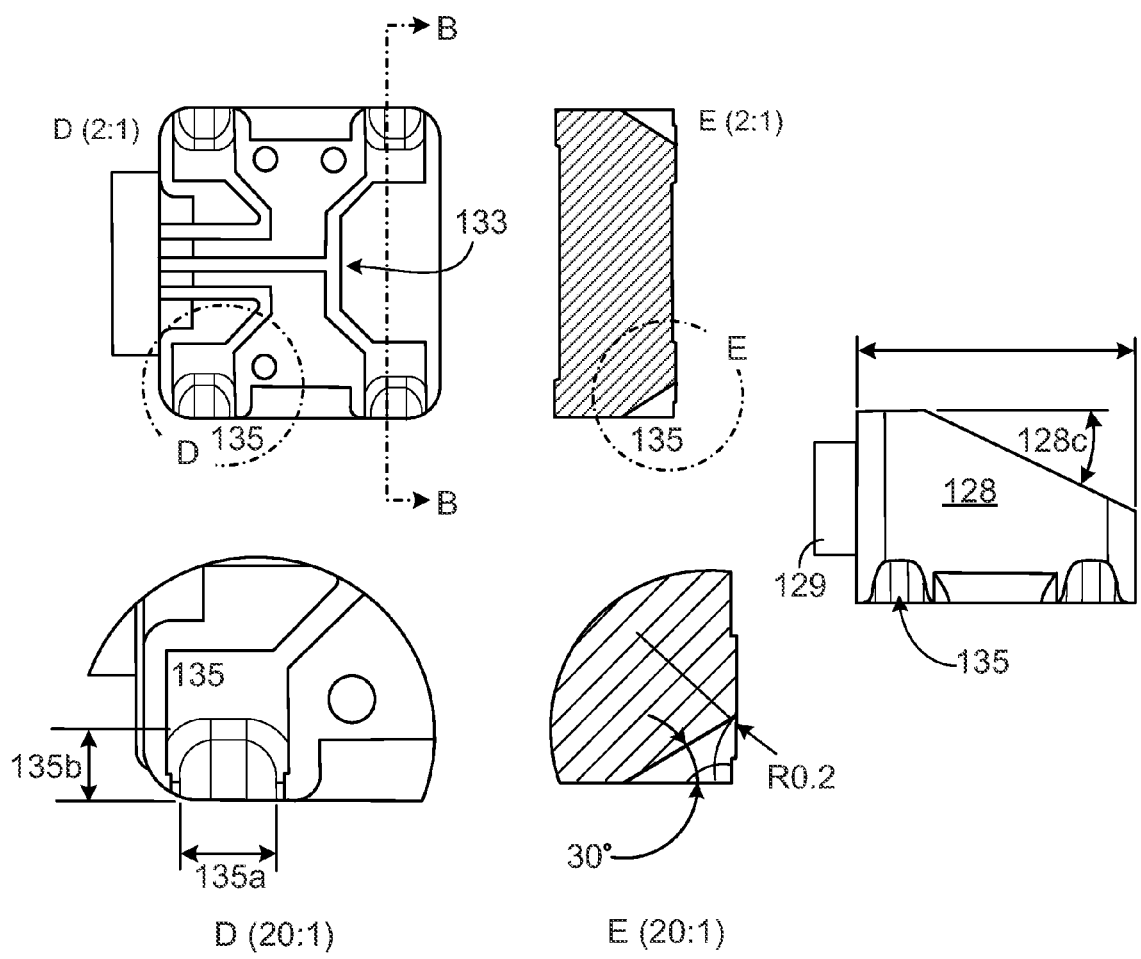

HALL SENSOR MOUNTING IN AN IMPLANTABLE BLOOD PUMP

CROSS-REFERENCE TO RELATED APPLICATIONS

This application claims priority to and the full benefit of U.S. Provisional Application Ser. No. 61/695,624, filed Aug. 31, 2012. The entire contents of U.S. Provisional Application Ser. No. 61/695,624 are incorporated herein by reference.

The description relates to United States Published Application No. 2012/0046514, filed Aug. 18, 2011, now U.S. Pat. No. 9,091,271, issued Jul. 28, 2015, and titled "Implantable Blood Pump," the entire contents of which are incorporated herein by reference.

FIELD

This description relates to mounting a Hall sensor in an implantable blood pump.

BACKGROUND

Ventricular assist devices, known as VADs, are implantable blood pumps used for both short-term and long-term applications where a patient's heart is incapable of providing adequate circulation. For example, a patient suffering from heart failure may use a VAD while awaiting a heart transplant. In another example, a patient may use a VAD while recovering from heart surgery. Thus, a VAD can supplement a weak heart or can effectively replace the natural heart's function. VADs can be implanted in the patient's body and powered by an electrical power source inside or outside the patient's body.

SUMMARY

The present disclosure describes one or more general aspects, implementations or embodiments involving devices, systems and methods for mounting a Hall sensor in an implantable blood pump.

When monitoring or controlling an electromagnetically levitated rotating object, it is useful to have sensors placed about the circumference of the rotating object to monitor its angular position, angular velocity, and any offsets from its ideal rotating axis. Placing these sensors can be challenging from the perspective of locating each sensor axially symmetric to the other sensors and facilitating an assembly process that does not impose mechanical stresses on the sensor package electrical interconnects.

One or more of the following aspects of this disclosure can be embodied alone or in combination as methods that include the corresponding operations. One or more of the following aspects of this disclosure can be implemented alone or in combination in a molded interconnect device or in an implantable blood pump that perform operations according to the one or more of the following aspects. One or more of the following aspects of this disclosure can be implemented alone or in combination in a molded interconnect device or in an implantable blood pump that includes parts according to the one or more of the following aspects.

In aspect 1, a molded interconnect device carrying a Hall sensor for transducing a position of a rotor of an implantable blood pump, the molded interconnect device is comprising: one or more integrated electronic circuit traces configured to electrically connect the hall sensor with a printed circuit board of the implantable blood pump, wherein the molded interconnect device is configured to be mounted to the printed circuit board.

Aspect 2 according to aspect 1, wherein the molded interconnect device further comprises: at least one recess on a surface of the device, the surface being oriented towards the printed circuit board or facing the printed circuit board.

Aspect 3 according to aspect 2, wherein the recess is configured to be at least partially filled with an adhesive.

Aspect 4 according to aspect 3, wherein the adhesive is configured to mount the molded interconnect device to the printed circuit board during the operation of the pump.

Aspect 5 according to any one of aspects 2 to 4, wherein the recess is adapted to be form-fit with a soldered joint that electrically connects the printed circuit board with the one or more integrated electronic circuit traces of the molded interconnect device.

Aspect 6 according to any one of aspects 3 to 5, wherein the adhesive is applied between the hall sensor and the printed circuit board and/or between a surface of the device and the printed circuit board.

Aspect 7 according to any one of aspects 1 to 6, wherein the molded interconnect device is configured to be attached on the printed circuit board between pole pieces of a stator of the pump.

Aspect 8 according to any one of aspects 1 to 7, wherein the hall sensor is configured to output a voltage that is directly proportional to a strength of a magnetic field that is located in a proximity of pole pieces of a stator of the pump and the rotor of the pump.

Aspect 9 according to an implantable blood pump, the pump comprising: a housing defining an inlet opening and an outlet opening; a dividing wall within the housing defining a blood flow conduit, the blood flow conduit extending between the inlet opening and the outlet opening of the housing; a rotary motor including a stator and a rotor, the stator being disposed within the housing circumferentially about the dividing wall such that the blood flow conduit extends through the stator, the stator being disposed circumferentially about at least a part of the rotor and being positioned relative to the rotor such that in use blood flows within the blood flow conduit through the stator before reaching the rotor, and the rotor having permanent magnetic poles for magnetic levitation of the rotor; and a molded interconnect device carrying a Hall sensor, the Hall sensor being configured to transduce a position of the rotor.

Aspect 10 according to aspect 9, wherein the molded interconnect device is mounted on a printed circuit board of the rotary motor between pole pieces of the stator.

Aspect 11 according to any one of aspects 9 to 10, wherein the molded interconnect device comprises one or more integrated electronic circuit traces that are configured to electrically connect the hall sensor with the printed circuit board.

Aspect 12, combinable with any one of aspects 1 to 11 or with any one of aspects 13 to 20, wherein the stator includes a first coil for driving the rotor and a second coil for adjusting a radial position of the rotor, the first coil and the second coil being wound around one or more of the pole pieces of the stator.

Aspect 13 according to any one of aspects 9 to 12, further comprising: at least one recess on a surface of the molded interconnect device, the surface being oriented towards the printed circuit board or facing the printed circuit board.

Aspect 14 according to aspect 13, wherein the recess is configured to be at least partially filled with an adhesive, and wherein the adhesive is adapted to secure the molded interconnect device to the printed circuit board during operation of the pump after being applied between the hall sensor and the printed circuit board and/or after being applied between the surface of the molded interconnect device and the printed circuit board.

Aspect 15 according to any one of aspects 13 to 14, wherein the recess is adapted to be form-fit with a soldered joint that electrically connects the printed circuit board with the one or more integrated electronic circuit traces of the molded interconnect device.

Aspect 16 according to any one of aspects 9 to 15, wherein the hall sensor is configured to output a voltage that is directly proportional to a strength of a magnetic field that is located in a proximity of the pole pieces and the rotor of the pump.

Aspect 17 according to any one of aspects 1 to 16, further comprising: an active electromagnetic control system configured to radially center the rotor within a blood flow conduit if the position transduced by the hall sensor is outside a predefined volume within the blood flow conduit.

Aspect 18, combinable with any one of aspects 1 to 17, is a method of assembling a blood pump, the method comprising: assembling a motor stator and control electronics in a housing circumferentially about an internal dividing wall, the internal dividing wall defining the a blood flow conduit that extends from an inlet opening to an outlet opening of the housing, the stator being assembled in the housing such that the blood flow conduit extends through the motor stator; disposing a magnetically-levitated rotor within the blood flow conduit and surrounded by the stator such that impeller blades carried by the rotor are downstream of the rotor from the inlet opening, and such that, in use, the impeller pumps blood from the inlet opening to the outlet opening through the stator; mounting a molded interconnect device between pole pieces of the motor stator onto a printed circuit board of the motor stator, wherein the molded interconnect device carries a Hall sensor that is configured to transduce a position of the rotor; and electrically connecting the Hall sensor with the printed circuit board and electrically connecting the printed circuit board with the control electronics.

Aspect 19 according to aspect 18, wherein the molded interconnect device is being placed on the printed circuit board by an insertion machine.

Aspect 20 according to any one of aspects 9 to 19, wherein the molded interconnect device is in accordance with any one of the aspects 1 to 8.

The following general aspects may be combinable with any one of the aspects 1 to 20.

In one general aspect, an implantable blood pump includes a housing and a blood flow conduit. Within the housing, the blood pump includes a stator located about the blood flow conduit and a magnetically-levitated rotor.

In another general aspect, an implantable blood pump includes a housing defining an inlet opening and an outlet opening. Within the housing, a dividing wall defines a blood flow conduit extending between the inlet opening and the outlet opening of the housing. The blood pump has a rotary motor that includes a stator and a rotor. The stator is disposed within the housing circumferentially about the dividing wall such that the inner blood flow conduit extends through the stator.

In another general aspect, an implantable blood pump includes a puck-shaped housing having a first face defining an inlet opening, a peripheral sidewall, and a second face opposing the first face. The blood pump has an internal dividing wall defining an inner blood flow conduit extending between the inlet opening and an outlet opening of the housing. The puck-shaped housing has a thickness from the first face to the second face that is less than a width of the housing between opposing portions of the peripheral sidewall. The blood pump also has a motor having a stator and a rotor. The stator is disposed in the housing circumferentially about the blood flow conduit and includes magnetic levitation components operable to control an axial position and a radial position of the rotor. The rotor is disposed in the inner blood flow conduit and includes an impeller operable to pump blood from the inlet opening to the outlet opening through at least a portion of the magnetic levitation components of the stator.

Implementations of the above aspects may include one or more of the following features. For example, the stator is disposed circumferentially about at least a part of the rotor and is positioned relative to the rotor such that in use blood flows within the blood flow conduit through the stator before reaching the rotor. The rotor has permanent magnetic poles for magnetic levitation of the rotor. A passive magnetic control system is configured to control an axial position of the rotor relative to the stator, and an active electromagnetic control system is configured to radially center the rotor within the inner blood flow conduit. An electromagnetic control system controls at least one of a radial position and an axial position of the rotor relative to the stator, and the electromagnetic control system has control electronics located within the housing about the dividing wall.

The control electronics are located between the inlet opening and the stator. The control electronics can be configured to control the active magnetic control system. The rotor has only one magnetic moment. The stator includes a first coil for driving the rotor and a second coil for controlling a radial position of the rotor, and the first coil and the second coil are wound around a first pole piece of the stator. The housing has a first face that defines the inlet opening, a second face opposing the first face, and a peripheral wall extending from the first face to the second face. The housing includes a rounded transition from the second face to the peripheral wall. The housing defines a volute located such that in use blood flows within the blood flow conduit through the stator before reaching the volute. The volute can be located between the stator and the second face. The housing can also include a cap that includes the second face, defines at least part of the volute, and defines at least part of the outlet. The cap is engaged with the peripheral wall of the housing. The housing also includes an inlet cannula extending from the first face and in fluid communication with the inlet opening. The inlet cannula can be inserted into the patient's heart. The outlet opening is defined in the second face and/or the peripheral wall. A thickness of the housing between the first face and the second face is less than a width of the housing.

In another general aspect, a method includes inserting a puck-shaped blood pump housing into a patient's body. The blood pump is inserted such that an opening defined in a first flat face of the housing that is proximate to a stator of the blood pump faces the patient's heart. Additionally, the blood pump is inserted such that a second rounded face of the housing that is proximate to an impeller of the blood pump faces away from the patient's heart. The first face is disposed against a portion of the patient's heart such that the second face of the housing faces away from the heart of the patient. In some implementations, the method includes inserting an inlet cannula of the housing into the patient's heart.

In another general aspect, making a blood pump includes assembling a motor stator and control electronics in a puck-shaped housing circumferentially about an internal dividing wall. The internal dividing wall defines an inner blood flow conduit that extends from an inlet opening to an outlet opening of the housing. The stator is assembled in the housing such that the inner blood flow conduit extends through the motor stator. Disposed within the inner blood flow conduit is a magnetically-levitated rotor. The rotor is surrounded by the stator such that impeller blades carried by the rotor are downstream of the stator from the inlet opening. In use, the impeller pumps blood from the inlet opening to the outlet opening through the stator.

Implementations may include one or more of the following features. For example, the rotor has only one magnetic moment. The stator includes at least one first coil for driving the rotor and at least one second coil for controlling a radial position of the rotor, the at least one first coil and the at least one second coil being wound around a first pole piece of the stator. The housing includes a first face that defines the inlet opening, and further comprising engaging an end cap with a peripheral wall of the housing, the end cap including a second face, defining at least part of a volute, and defining at least part of the outlet opening. The housing includes a rounded transition from the second face to the peripheral wall. The housing further includes an inlet cannula extending from the first face and in fluid communication with the inlet opening. A thickness of the housing between the first face and the second face is less than a width of the housing.

In another general aspect, a method of pumping blood includes magnetically rotating a centrifugal pump impeller of a blood pump device to draw blood from a patient's heart through an inlet opening of a housing of the blood pump device into an inner blood flow conduit within a stator in the housing, through the inner blood flow conduit, and through an outlet opening of the housing. The method includes selectively controlling a radial position of the impeller within the inner blood flow conduit.

In another general aspect, a sensor mount assembly includes a printed circuit board having rigid and flexible portions, sensors having rigid material attached thereto, and a carrier for supporting the printed circuit board and the sensors. The carrier has rails to locate the rigid material attached to the sensors.

The details of one or more of these and other aspects, implementations or embodiments are set forth in the accompanying drawings and the description below. Other features, aims and advantages will be apparent from the description and drawings, and from the claims.

DESCRIPTION OF THE DRAWINGS

FIG. 7 is a top perspective view and side perspective view of an exemplary hall sensor in bump design.

FIG. 8 is a top perspective view and side perspective view of an exemplary hall sensor in via design.

FIG. 9 is a top perspective view and side perspective view of an exemplary hall sensor in pocket design.

Reference numbers and designations in the various drawings indicate exemplary aspects, implementations or embodiments of particular features of the present disclosure.

DETAILED DESCRIPTION

This description relates to mounting a Hall sensor in an implantable blood pump.

The subject matter described in this disclosure can be implemented in particular aspects or embodiments so as to realize one or more of the following advantages.

First, a molded interconnect device may allow a Hall sensor to be positioned at an adequate position within the blood pump, while the device may be inserted into the pump with insertion machines employed for the assembly of the pump. For example, the implementations or aspects described herein allow a Hall sensor to be positioned and mounted on a printed circuit board of a stator of the pump thereby allowing the Hall sensor to transduce a position of a rotor during operation of the pump.

Second, mechanical stress on integrated electronic conductive traces of the molded interconnect device may be reduced and may thereby enhance the robustness of a connection between the device and a printed circuit board. In general, particular aspects described herein may provide improved robustness of the device carrying the Hall sensor on the board and within the pump, e.g. for halt or break off test of the motor of the pump.

Third, the molded interconnect device carrying the Hall sensor may allow adhesives to be easily employed to further enhance the stability of the Hall sensor in the pump.

Fourth, the force applied to a soldered joint between the printed circuit board and the molded interconnect device during operation of the pump may be reduced, e.g. the force may a centrifugal force, a shear force and/or a frictional force.

Other advantages of this disclosure will be apparent to those skilled in the art.

Figure 1:
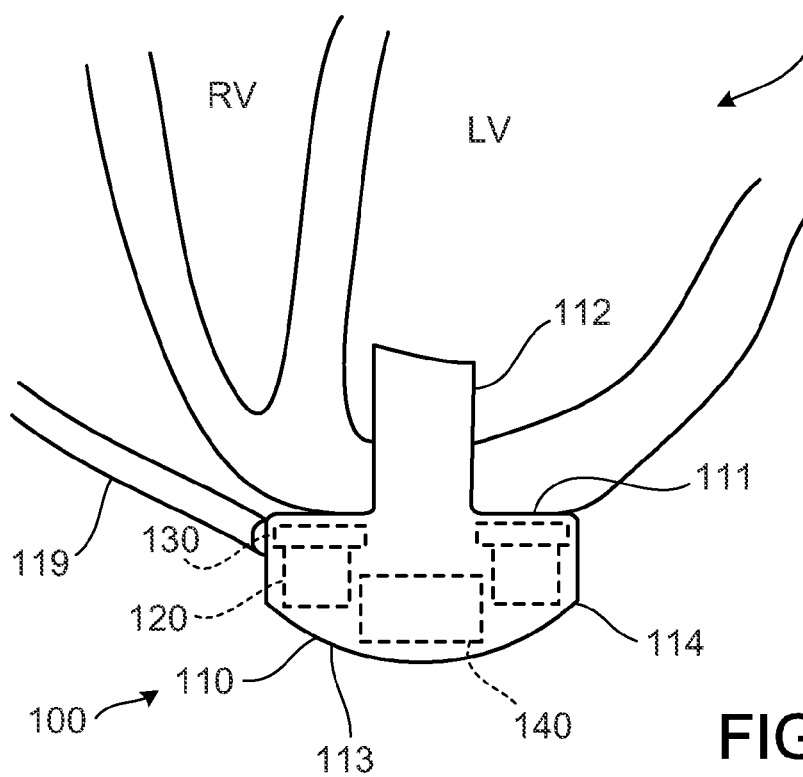
FIG. 1 is an illustration of a blood pump in a use position implanted in a patient's body.
Figure 4:
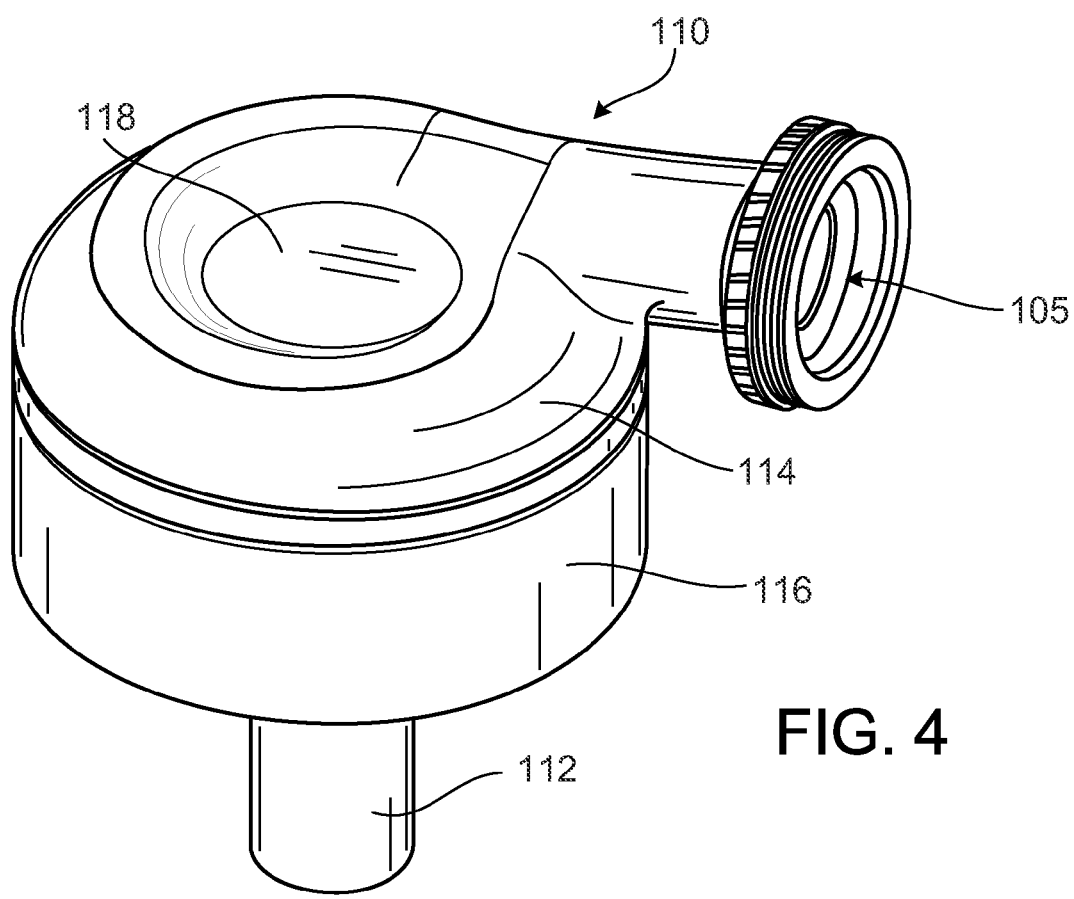
FIG. 4 is a bottom perspective view of a blood pump.
Figure 5:
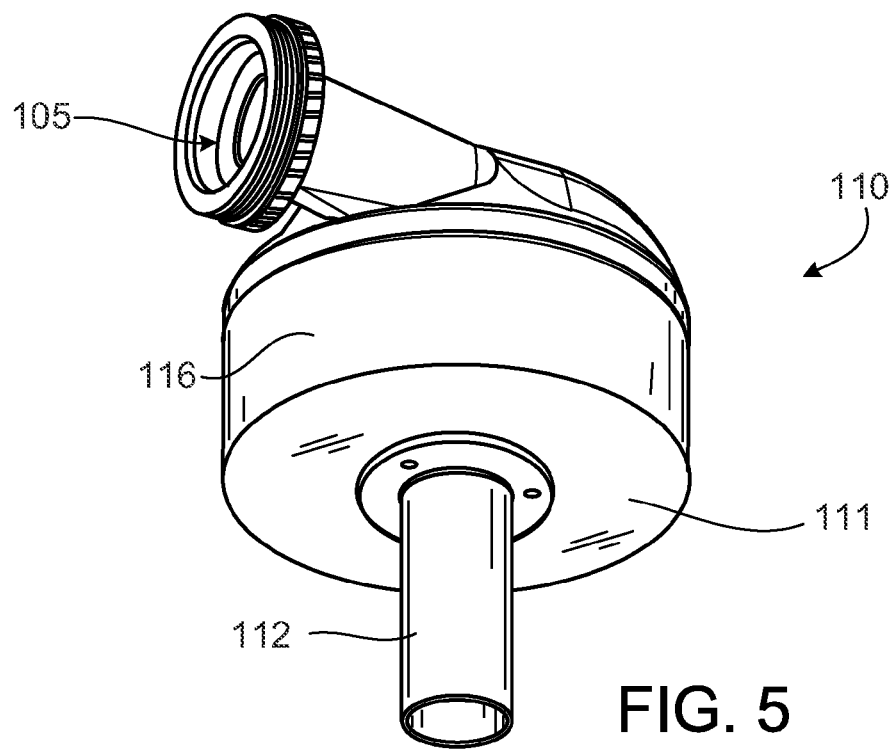
FIG. 5 is a top perspective view of the blood pump of FIG. 4.

With reference to FIGS. 1, 4 and 5, a left ventricular assist blood pump 100 having a puck-shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump 100, such as the patient's diaphragm. To construct the illustrated shape of the puck-shaped housing 110 in a compact form, a stator 120 and electronics 130 of the pump 100 are positioned on the inflow side of the housing toward first face 111, and a rotor 140 of the pump 100 is positioned along the second face 113. This positioning of the stator 120, electronics 130, and rotor 140 permits the edge 114 to be chamfered along the contour of the rotor 140, as illustrated in at least FIGS. 2, 4, and 5, for example.

Figure 2:
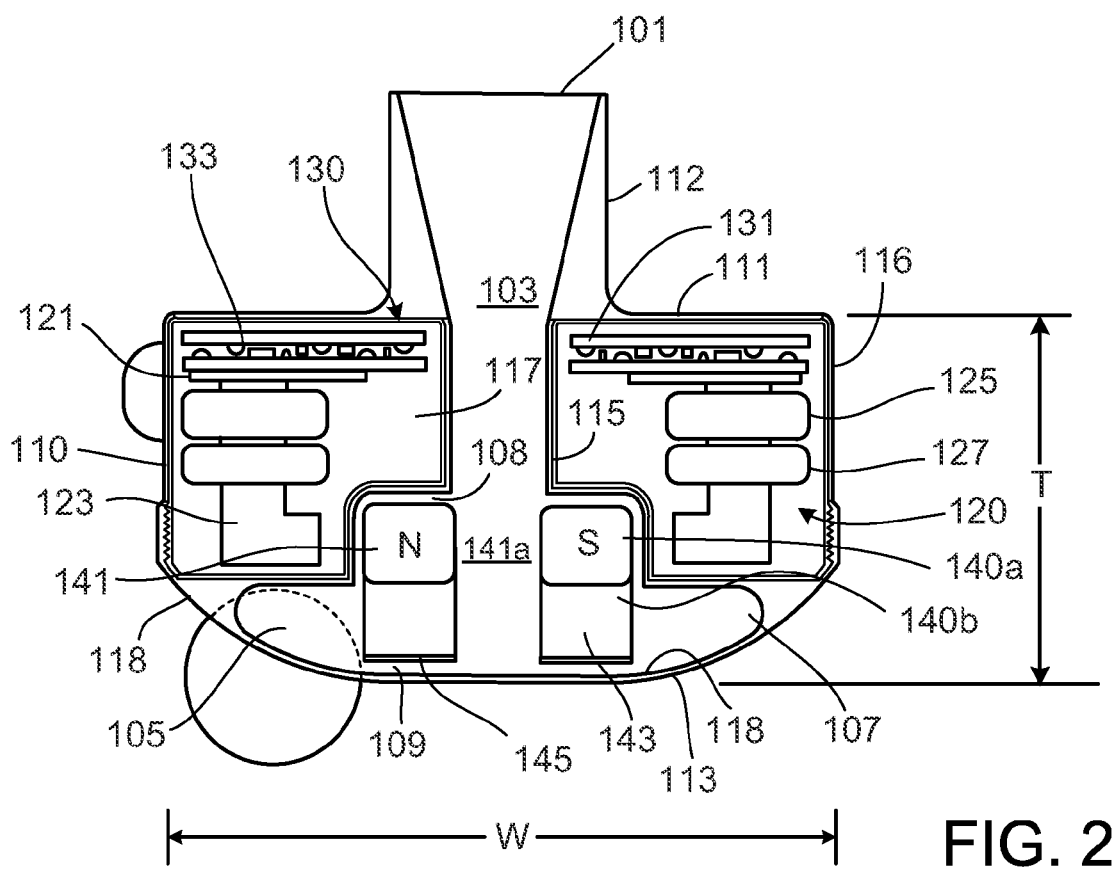
FIG. 2 is a cross-sectional view of the blood pump of FIG. 1.

Referring to FIG. 2, the blood pump 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components 133 carried on the circuit boards 131 to control the operation of the pump 100 by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

Figure 3:
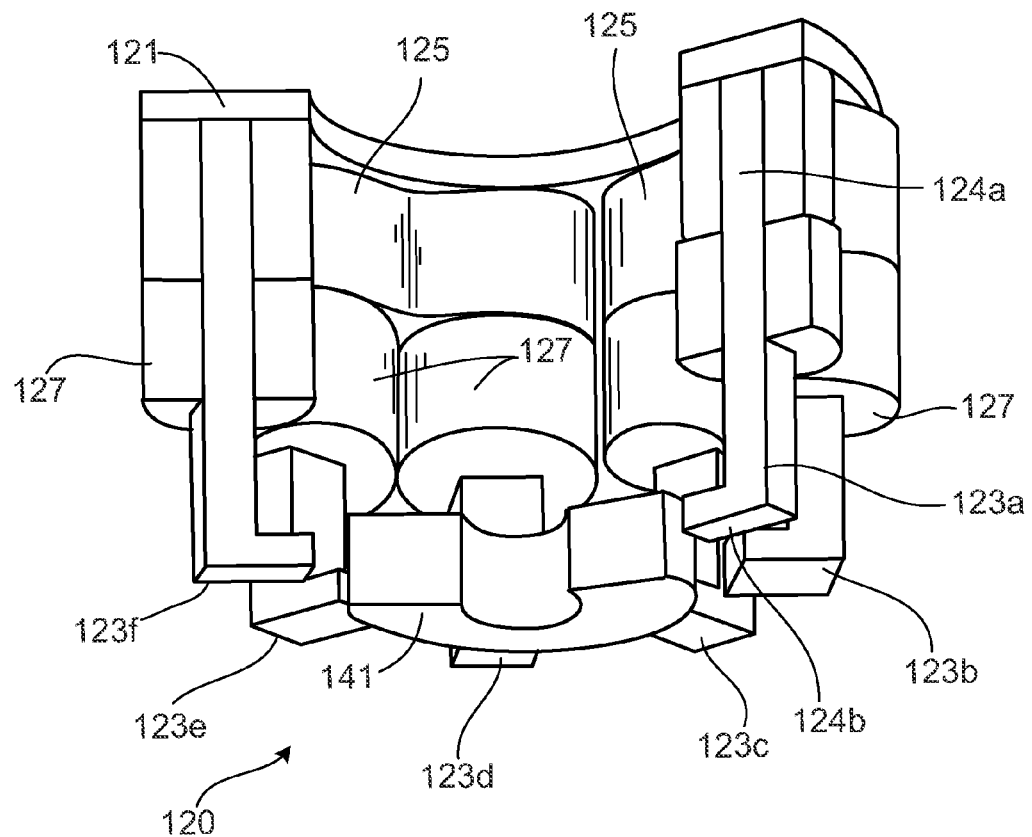
FIG. 3 is a partial cut-away perspective view of a stator of a blood pump.
Figure 3:
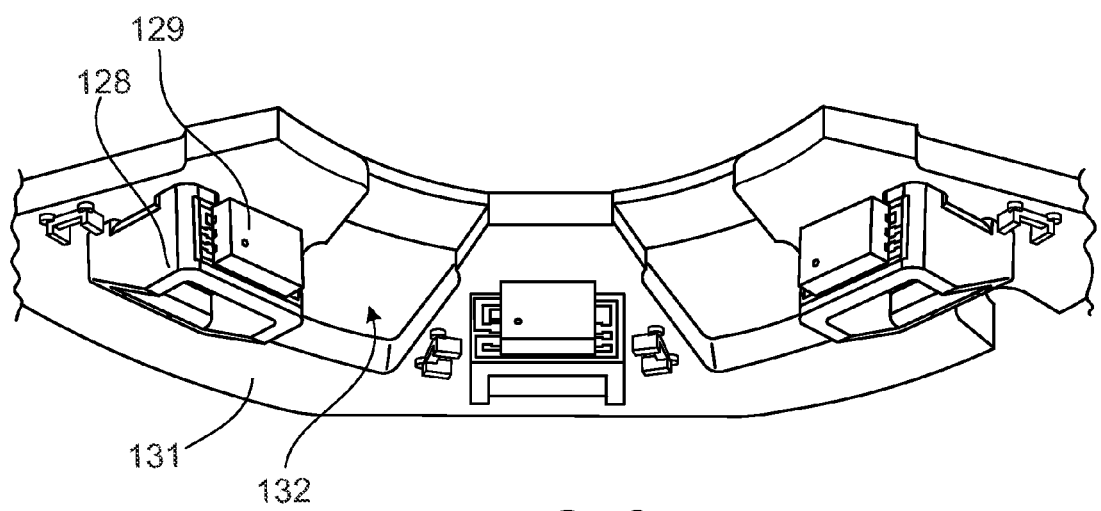

With continued reference to FIG. 2 and with reference to FIG. 3, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a may also have a second leg 124b that extends from the first leg 124a through an opening 132 of a printed circuit board 131 towards the dividing wall 115 proximate the location of the permanent magnet 141 of the rotor 140. In an aspect, each of the second legs 124b of the pole pieces 123a-123f is sticking through an opening 132 of the printed circuit board 131. In an aspect, each of the first legs 124a of the pole pieces 123a-123f is sticking through an opening 132 of the printed circuit board 131. In an aspect, the openings 132 of the printed circuit board are enclosing the first legs 124a of the pole pieces 123a-123f.

In an aspect, at least one molded interconnect device 128 is mounted on the printed circuit board of the pump 100, e.g. the at least one molded interconnect device 128 is mounted on the printed circuit board of the stator 120. In an aspect, the molded interconnect device 128 comprises a Hall sensor 129, e.g., the molded interconnect device 128 carries the Hall sensor 129. For example, the molded interconnect device 128 may be mounted on the printed circuit board 131 via one or more of integrated electric circuit traces, soldered joint and adhesive. For example, the molded interconnect device 128 may be mounted to the printed circuit board 131 using an epoxy or liquid polymer crystals as the adhesive. For instance, the molded interconnect device 128 may be glued to the printed circuit board 131.

In an aspect, the epoxy is a rapid curing, fast flowing, liquid epoxy for use as capillary flow underfill on printed circuit boards, wherein when the epoxy is fully cured, it may reduce (e.g., minimize) induced stress at solder joints between the printed circuit board 131 and the molded interconnect device 128. For example, the adhesive may improve a thermal cycling performance of the printed circuit board 131, the molded interconnect device 128 and/or the soldered joints. In an aspect, the adhesive provides the functionality of an underfill between the printed circuit board 131 and the at least one molded interconnect device 128. For example, the adhesive may be applied (e.g., as underfill) between the Hall sensor 129 and the printed circuit board 131 and/or between the printed circuit board 131 and the molded interconnect device 128.

In a general aspect, the Hall sensor 129 may be configured to transduce a position of the rotor 140 of the pump 100. For example, the Hall sensor may be in upright position on the printed circuit board 131. For instance, the Hall sensor may be standing orthogonally on the printed circuit board 131. For example, a longest edge of the Hall sensor may be aligned to possess an orthogonal component with respect to the surface of the printed circuit board 131. In a general aspect, the Hall sensor 129 may be adapted to sense a position of the rotor 140 of the pump 100. For example, the Hall sensor 129 may provide an output voltage, which is directly proportional to a strength of a magnetic field that is located in between at least one of the pole pieces 123a-123f and the permanent magnet 141. For example, the Hall sensor 129 may provide an output voltage, which is directly proportional to a strength of a magnetic field that is located in a proximity of at least one of the pole pieces 123a-123f and the rotor 140 of the pump 100. For example, the Hall sensor 129 may provide an output voltage, which is directly proportional to a strength of a magnetic field that is located in between at least one of the pole pieces 123*a*-123*f* and the permanent magnet 141, and wherein the output voltage is directly proportional to a current flowing in the Hall sensor 129.

In a general aspect, the Hall sensor 129 may provide an output voltage, which is directly proportional to a strength of a magnetic field that is located in between at least one of the pole pieces 123*a*-123*f* and the permanent magnet 141, and the output voltage may provide feedback to the control electronics 130 of the pump 100 to determine if the rotor 140 and/or the permanent magnet 141 is not at its intended position for the operation of the pump 100. For example, a position of the rotor 140 and/or the permanent magnet 141 may be adjusted, e.g. the rotor 140 or the permanent magnet 141 may be pushed or pulled towards a center of the blood flow conduit 103 or towards a center of the stator 120.

Each of the pole pieces 123*a*-123*f* also has a levitation coil 127 for generating an electromagnetic field to control the radial position of the rotor 140. Each of the drive coils 125 and the levitation coils 127 includes multiple windings of a conductor around the pole pieces 123*a*-123*f*. Particularly, each of the drive coils 125 is wound around two adjacent ones of the pole pieces 123, such as pole pieces 123*d* and 123*e*, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein for all purposes by reference. The control electronics 130 and the stator 120 receive electrical power from a remote power supply via a cable 119 (FIG. 1). Further related patents, namely U.S. Pat. No. 5,708,346, U.S. Pat. No. 6,053,705, U.S. Pat. No. 6,100,618, U.S. Pat. No. 6,879,074, U.S. Pat. No. 7,112,903, U.S. Pat. No. 6,278,251, U.S. Pat. No. 6,278,251, U.S. Pat. No. 6,351,048, U.S. Pat. No. 6,249,067, U.S. Pat. No. 6,222,290, U.S. Pat. No. 6,355,998 and U.S. Pat. No. 6,634,224, are incorporated herein for all purposes by reference in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124*b* of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118*a* of the cap 118. The rotor 140 also includes a shroud 145 that covers the ends of the impeller blades 143 facing the second face 113 that assists in directing blood flow into the volute 107. The shroud 145 and the inner surface 118*a* of the cap 118 form a gap 109 between the shroud 145 and the inner surface 118*a* when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141*a* formed through the permanent magnet 141. Blood also flows through the gap 108 between the rotor 140 and the dividing wall 115 and through the gap 109 between the shroud 145 and the inner surface 108*a* of the cap 118. The exemplary gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the exemplary gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the exemplary rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the Hall sensor 129 may sense a current position of the rotor 140 and/or the permanent magnet 141, wherein the output voltage of the Hall sensor 129 may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141*a* of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118*a* of the cap 118. The blood exits the volute 107 through the outlet opening 105.

Figure 6:
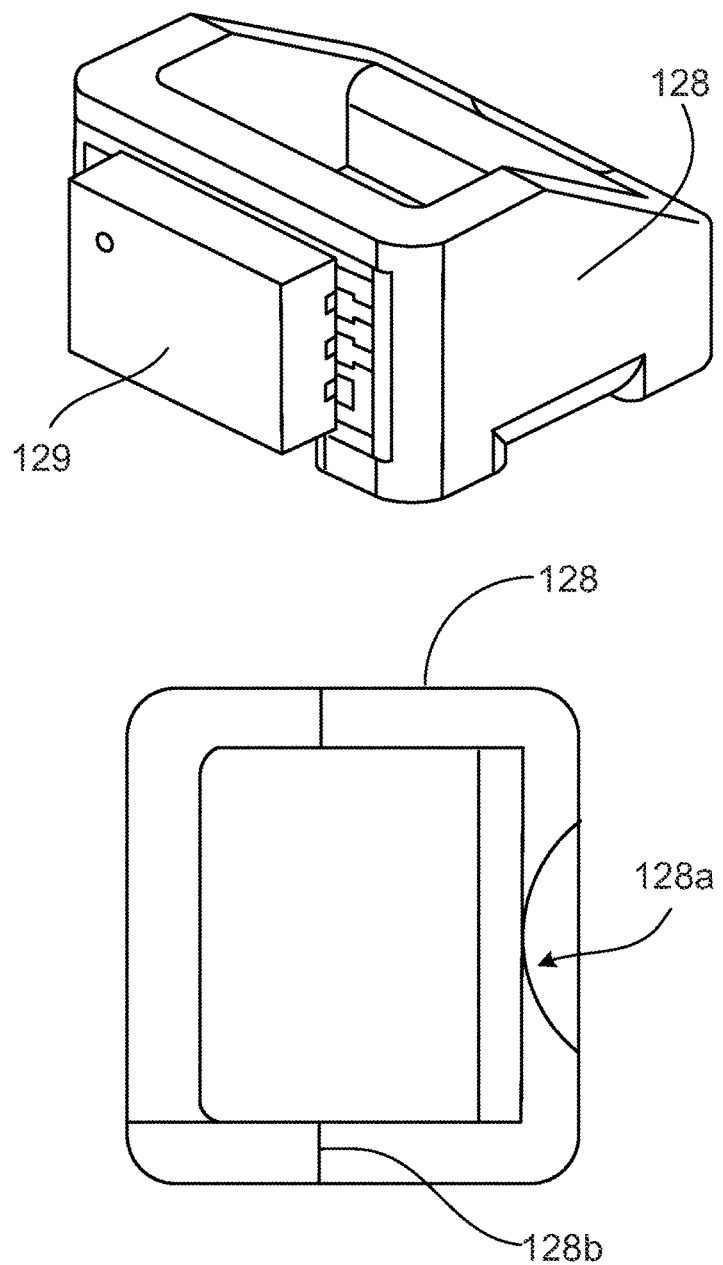
FIG. 6 is a bottom perspective view and side perspective view of an exemplary hall sensor of FIG. 3.

FIG. 6 describes a bottom and side view of an exemplary molded interconnect device 128 according to an aspect described herein. The molded interconnect device 128 may carry the Hall sensor 129 on one surface of the molded interconnect device 128, wherein the Hall sensor may be electrically connected with the molded interconnect device 128 via one or more integrated electronic circuit traces 133. In an aspect, the Hall sensor 129 may be located inside the device 128 or may be partially enclosed by the device 128. The bottom of the molded interconnect device 128 is facing the bottom side of the pump 100. The top of the molded interconnect device 128 is facing the printed circuit board 131 of the pump 100. The bottom perspective of the molded interconnect device is illustrated in FIG. 6 (lower illustration). The molded interconnect device 128 may possess a cut-out 128*a*, wherein film gate material may be removed. In an aspect, a thickness 128*b* of walls of the molded interconnect device 128 may be adapted for the molded interconnect device 128 to be aligned on the printed circuit board 131 with an automated assembly machine, wherein the automated assembly machine may also be used to assemble the printed circuit board 131 and/or the stator 120 of the pump 100. For example, the thickness 128*b* may be below 1 millimeter, preferentially about 0.7 millimeters.

In a general aspect, to make the molded interconnect device 128 more robust one or more of the followings actions are taken. An adhesive (e.g. an underfill material) is applied between the Hall sensor 129 and a surface of the molded interconnect device 128 and/or between a surface of the molded interconnect device 128 and the printed circuit board 131. This particular aspect or implementation may limit force flow through the integrated circuit traces and rather leads the forces directly through the adhesive into the printed circuit board 131. Additionally and in an example, the adhesive may be easily implemented with the printed circuit board assembly and manufacturing process. In a further aspect, the molded interconnect device 128 may be designed with recesses (e.g., pockets) that enable a form fit between the molded interconnect device 128 and soldered joints of the printed circuit board 131. In an aspect, laser parameters for structuring the molded interconnect device 128 may be optimized and a width of the integrated electronic circuit traces may be increased. In general, in blood pumps, mechanical forces may be generated due to thermal expansion and metallized traces or joints may become separated from their supporting material, wherein the metallized traces may experience a fracture during pump operation. In a general aspect, halt tests and/or break off tests of the motor were performed and rendered one or more of the following designs of the molded interconnect device 128 particularly mechanically robust during operation of the pump.

FIG. 7 describes an exemplary top and side view of a hall sensor in a bump design according to one or more aspects of the present disclosure. The molded interconnect device 128 carries a Hall sensor 129 and includes multiple integrated electronic circuit traces 133, wherein one or more bumps 132 may be added to the traces 133. This particular aspect may reduce mechanical stress on the traces 133, e.g., by using a mechanical form fit. In an aspect, the size of the bump 132 may be below 1 millimeters, preferentially be 0.73 millimeters. For example, the molded interconnect device 128 may include four bumps that are located at each corner of one surface of the device 128, wherein the surface is facing the printed circuit board 131 when the device 128 is mounted on the printed circuit board 131.

FIG. 8 describes an exemplary top and side view of a Hall sensor in a via design according to one or more aspects of the present disclosure. The molded interconnect device 128 carries a Hall sensor 129 and includes one or more integrated electronic circuit traces 133, wherein one or more electrically conductive pins 134 may each include at least one via 134*a*. In an example, the pins 134 may be a part of the traces 133. This particular implementation may increase a strength of the connection between the traces 133 and the molded interconnect device 128 by implementing the via 134*a* that may extend through a wall of the device 128. For example, the via 134*a* is a hole or a hollow channel extending through the wall of the molded interconnect device 128. For example, the pins 134 may be soldered to the printed circuit board 131 thereby electrically connecting the Hall sensor 129 with the board 131.

FIG. 9 describes an exemplary top and side view of a Hall sensor in a pocket design according to one or more aspects of the present disclosure. The molded interconnect device 128 carries a Hall sensor 129 and includes one or more integrated electronic circuit traces 133, wherein one or more electrically conductive recesses 135 or pockets 135 may be located at one or more surfaces of the device 128. For example, the recess or pocket 135 may be an electrically conductive pin that is formed by a cut-out of a wall of the device 128. For instance, the recess or pocket 135 may be formed by cutting-out a fraction of a wall of the molded interconnect device 128. For instance, the fraction may be cut out at a corner of the device 128, wherein the corner is facing the printed circuit board 131 when the device 128 is mounted on the board 131. In an aspect, the width 135*b* of the recess 135 may be less than 1 millimeter, preferentially 0.6 millimeter. In an aspect, the length 135*a* of the recess 135 may be less than 1 millimeter, preferentially 0.8 millimeter. In an aspect, the height of the recess 135 may be less than 1 millimeter. In an aspect, the molded interconnect device is wedge- or trapeze-shaped with an apex angle 128*c* between 10 and 45 degrees, preferentially 25 degrees or 30 degrees.

In an aspect, the recess or pocket 135 may be form-fit with soldered joints, the soldered joints electrically and/or mechanically connecting the printed circuit board 131 with the integrated electronic circuit traces 133 of the molded interconnect device 128. For example, each recess or pocket 135 of the device 128 may at least partially enclose a soldered joint, the soldered joints electrically and/or mechanically connecting the printed circuit board 131 with the integrated electronic circuit traces 133 of the molded interconnect device 128. In an aspect, the recess or pocket 135 may be at least partially filled with an adhesive, which mounts the device 128 to the printed circuit board 131 and secures mounting of the molded interconnect device 128 to the printed circuit board 131 of the pump 100 during operation of the pump 100. The adhesive (e.g., a liquid epoxy) may be configured to perform capillary actions on the board 131 and flows into the recess or pocket 135 without an additional external force applied to the adhesive. The particular implementation described herein may remove forces applied to the traces 133 and/or the soldered joints during operation of the pump 100 and may guide these forces between the device 128 and the board 131 through the adhesive (e.g. underfill), wherein the forces may for example be centrifugal forces, shear forces and/or frictional forces.

The particular implementation of the pocket design described in the context of FIG. 9 may reduce mechanical stress on the traces 133 of the molded interconnect device 128 and may thereby enhance the robustness of a connection between the device 128 and the board 131. The particular implementation of the pocket design described herein may increase the stability of the integrated electronic circuit traces 133 of the molded interconnect device 128. The particular implementation of the pocket design described herein may increase the stability of the connection between the integrated electronic circuit traces 133 and the molded interconnect device 128. The particular implementation of the pocket design described herein may reduce the force applied to the integrated electronic circuit traces 133 of the molded interconnect device 128, e.g. the force may a centrifugal force, a shear force and/or a frictional force that may occur during operation of the implantable blood pump 100. The particular implementation of the pocket design described in the context of FIG. 9 may reduce the force applied to the soldered joint between the printed circuit board 131 and the molded interconnect device 128, e.g. the force may a centrifugal force, a shear force and/or a frictional force that may occur during operation of the implantable blood pump 100. In general, the particular implementations or aspects described in FIGS. 7, 8 and 9 may provide improved robustness of the device 128 on the board 131 within the pump 100, e.g. the robustness may be determined or classified by a halt or break off test of the motor of the pump 100.

In a general aspect, using silicone coating in a proximity of the molded interconnect device 128 on the printed circuit board 131 may be a buffer and may reduce mechanical stress on the device 128 and/or the Hall sensor 129.

In a general aspect, the width of the integrated electronic circuit traces 133 may be 0.2-0.25 millimeters. In an aspect, lead-free solder may be applied between the Hall sensor 129 and the molded interconnect device 128. In an aspect, the molded interconnect device 128 is directly soldered on the printed circuit board 131 of the pump 100.

Figure 10:
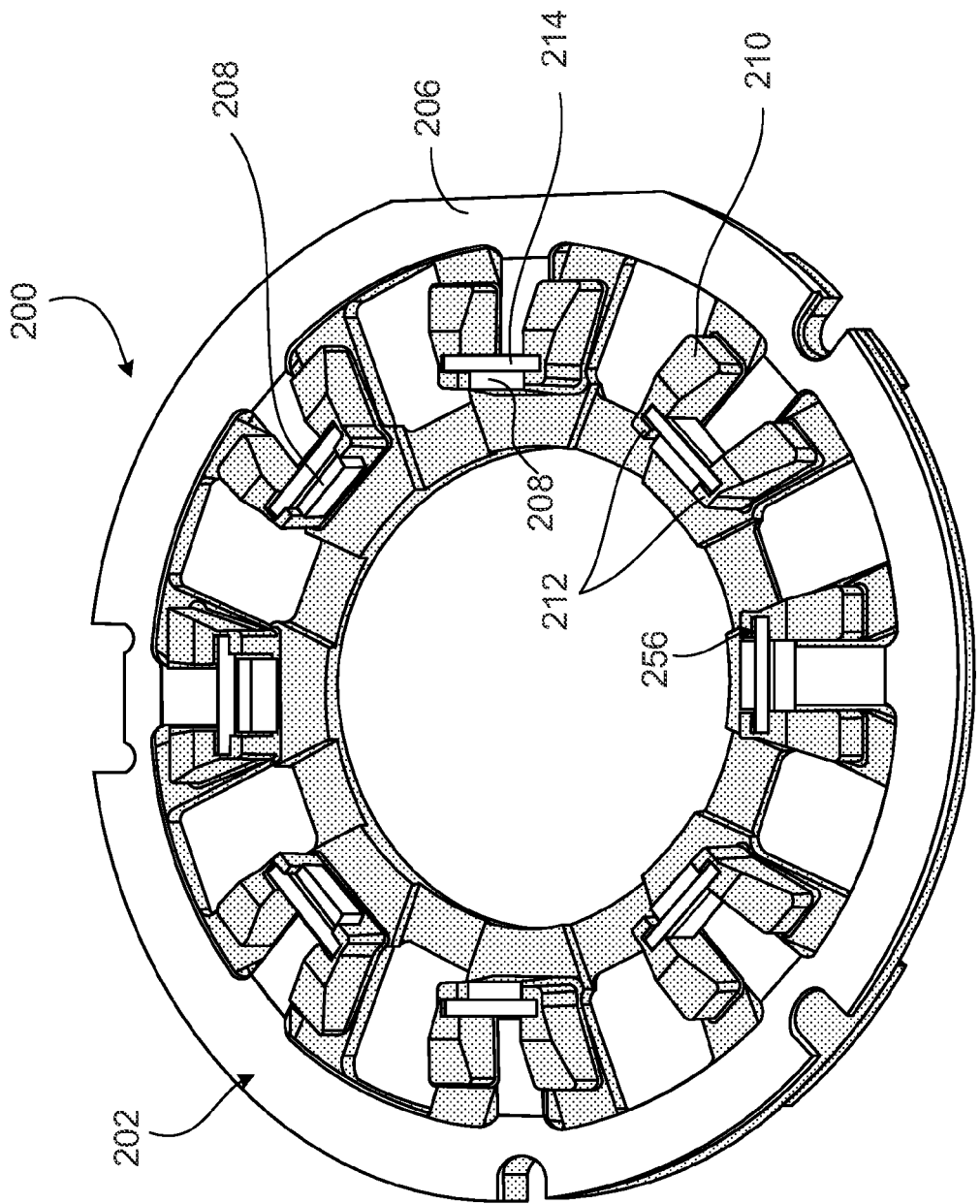
FIG. 10 is an illustration of an alternative embodiment of a sensor mount.
Figure 11:
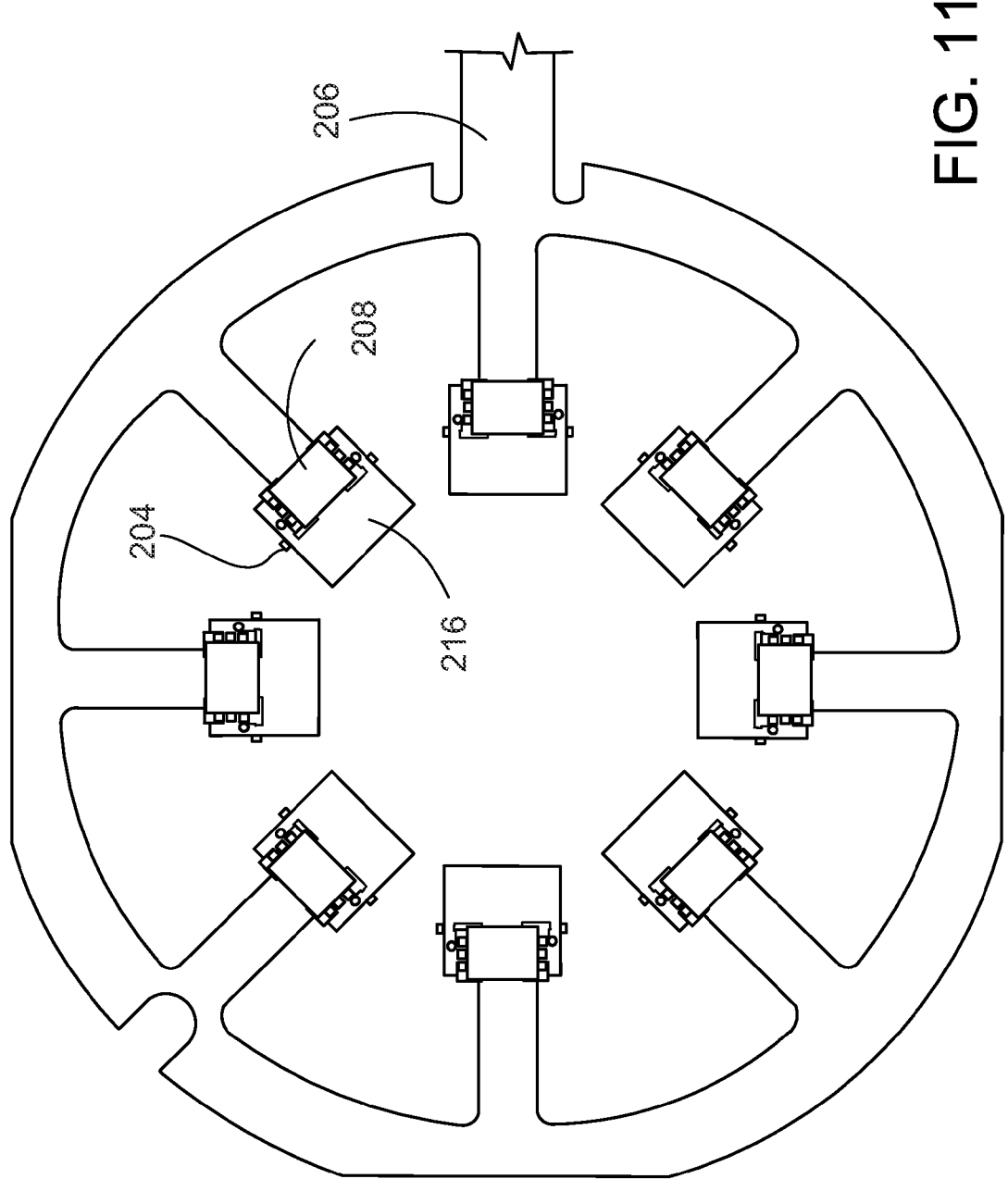
FIG. 11 is a top view of a rigid-flex PCB of the sensor mount of FIG. 10.

Referring to FIGS. 10 and 11, according to another embodiment of a sensor mount 200, a printed circuit board 202 having rigid 204 and flexible 206 portions provides mechanical compliance between the individual sensors 208 while maintaining a single set of soldered electrical interconnects between the sensor and the remainder of the system. As there is compliance in the flex circuit portion, mechanical positioning tolerances in the mechanical fixturing can be accommodated without placing excessive stress on the electrical interconnectors. Eight axi-symmetric sensors 208 are placed in a rigid, plastic mechanical carrier 210 and the Rigid-Flex PCB 202 is placed onto the carrier. The mechanical carrier uses guide rails 212 to locate electrically neutral rigid PCB portions 214 attached to the top edges of the sensors 208 and to locate the Rigid-Flex PCB 202. Excess rigid break-away tabs 216 of the rigid-flex PCB 202 (shown in FIG. 11) have been removed in FIG. 10.

Before the sensors are inserted into their mechanical retainers, the electrically neutral rigid PCB portions 214 are attached to their top edges. This rigid PCB portion allows the person or robot assembling the sensor unit to grab the rigid PCB supporting each sensor without causing mechanical damage to the sensor itself. In addition, this neutral portion of rigid PCB can be masked with a static dissipative coating that minimizes the change of electrostatic discharge (ESD) damage to the sensor IC.

Figure 12:
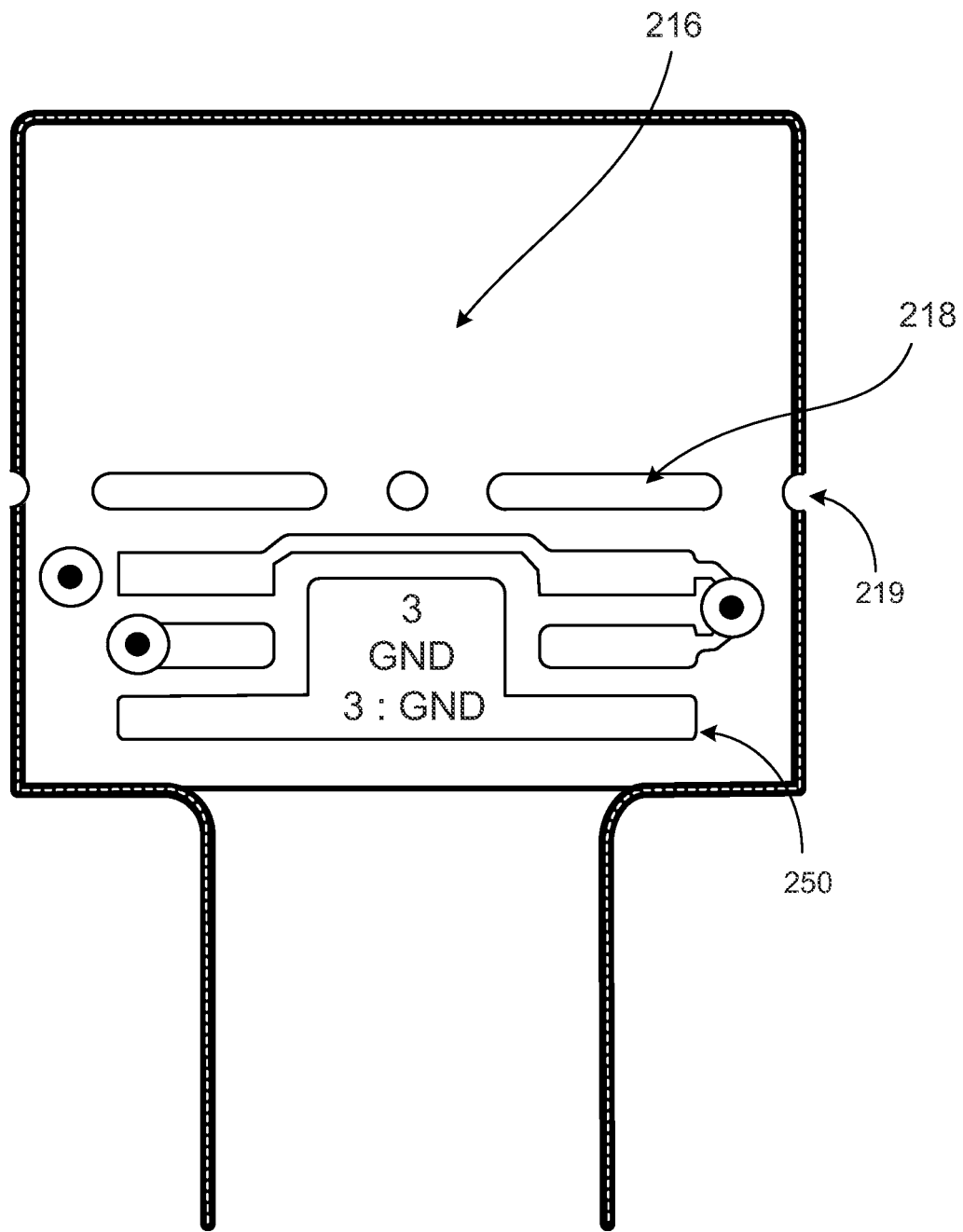
FIG. 12 illustrates a break-away tab of the rigid-flex PCT of FIG. 11.

Once the sensor is positioned in its mechanical fixture and soldered to the rigid portion 204 of the Rigid-Flex PCB 202, the excess portion 216 of the rigid PCB is broken off by the assembler, leaving a minimum amount of rigid PCB to support the sensor and allowing an overall smaller assembly. Referring to FIG. 12, the excess rigid PCB 216 is removed through the use of carefully positioned "break-away" scoring marks 218 and/or small holes 219 commonly called "mouse bites". These features provide a way of precisely locating the break-away transition and, during the break-away process, imparting minimum stress on the soldered electrical interconnects 250 joining the sensor to the remaining rigid PCB portion.

A number of implementations have been described. Nevertheless, it will be understood that various modifications may be made without departing from the spirit and scope of the claimed invention. For example, the cap 118 can be engaged with the peripheral wall 116 using a different attachment mechanism or technique, including snap-fit engagement, adhesives, or welding. Additionally, while the cap 118 has been described as defining the outlet opening 105 and the chamfered edge 114, the outlet opening 105 and/or the chamfered edge 114 can be defined by the peripheral wall 116 or by both the peripheral wall 116 and the cap 118. Similarly, the dividing wall 115 can be formed as part of the cap 118.

Additionally, the rotor 140 can include two or more permanent magnets. The number and configuration of the pole pieces 123 can also be varied. The operation of the control electronics 130 is selected to account for the number and position of pole pieces of the stator and permanent magnets of the rotor. Also, the cap 118 can be engaged with the peripheral wall using other techniques, such as adhesives, welding, snap-fit, shrink-fit, or other technique or structure. Similarly, the first face 111 may be formed from a separate piece of material than the peripheral wall 116 and the first face 111, including the inlet cannula 112, can be attached to the peripheral wall 116, such as by welding, after the control electronics 130 and the stator 120 have been mounted in the internal compartment 117. The shroud 145 may be omitted and optionally replaced by other flow control devices to achieve a desired pump efficiency. As another option, the control electronics 130 can be located external to the pump 100, such as in a separate housing implanted in the patient's abdomen, or external to the patient's body.

In some implementations, the dimensions of the housing 110 can be larger or smaller than those described above. Similarly, the ratio of the width W of the housing 110 to the thickness T of the housing can be different than the ratio described above. For example, the width W can be from about 1.1 to about 5 times greater than the thickness T. Additionally, the permanent magnet 141 of the rotor 140 can include two or more pairs of north and south magnetic poles. While the peripheral wall 116 and the dividing wall 115 are illustrated as cylinders having circular cross-sectional shapes, one or both can alternatively be formed having other cross-sectional shapes, such as oval, or an irregular shape.

Similarly, the peripheral wall 116 can be tapered such that the housing does not have a constant width W from the first face 111 to the second face 113.

As mentioned above, in some implementations, the blood pump 100 can be used to assist a patient's heart during a transition period, such as during a recovery from illness and/or surgery or other treatment. In other implementations, the blood pump 100 can be used to partially or completely replace the function of the patient's heart on a generally permanent basis. In a particular aspect described herein, the molded interconnect device 128 carrying the Hall sensor 129 may allow to monitor the position of the rotor of the pump 100 and may thereby help to ensure a proper operating status of the implantable blood pump 100.

The preceding figures and accompanying description illustrate example processes and example devices. But example Hall sensor 129 or molded interconnect device 128 (or other components) contemplates using, implementing, or executing any suitable technique for performing these and other tasks. It will be understood that these processes and parts are for illustration purposes only and that the described or similar techniques may be performed at any appropriate time, including concurrently, individually, in parallel, and/or in combination. In addition, many of the steps or parts in these processes may take place simultaneously, concurrently, in parallel, and/or in different orders than as shown. Moreover, molded interconnect device 128 may use components with additional parts, fewer parts, and/or different parts, so long as the devices remain appropriate. Moreover, although features may be described above as acting in certain combinations and even initially claimed as such, one or more features from a claimed combination can in some cases be excised from the combination, and the claimed combination may be directed to a sub-combination or variation of a sub-combination.

In other words, although this disclosure has been described in terms of certain aspects, implementations, examples or generally associated methods, alterations and permutations of these aspects, implementations or methods will be apparent to those skilled in the art. Accordingly, the above description of example aspects, implementations or embodiments do not define or constrain this disclosure. Other changes, substitutions, and alterations are also possible without departing from the spirit and scope of this disclosure.

What is claimed is:

1. A device for transducing a position of a rotor of an implantable blood pump, the device comprising:
   a molded interconnect device comprising one or more integrated electronic circuit traces, wherein the molded interconnect device is to be mounted to a printed circuit board; and
   a Hall sensor coupled to the molded interconnect device for transducing the position of the rotor, wherein the one or more integrated electronic circuit traces are configured to electrically connect the Hall sensor with the printed circuit board of the implantable blood pump.

2. The device of claim 1, wherein the molded interconnect device further comprises:
   at least one recess on a surface of the molded interconnect device, the surface being oriented towards the printed circuit board or facing the printed circuit board.

3. The device of claim 2, wherein the recess is configured to be at least partially filled with an adhesive.

4. The device of claim 3, wherein the adhesive is configured to secure the molded interconnect device to the printed circuit board during the operation of the pump.

5. The device of claim 2, wherein the recess is adapted to be form-fit with a soldered joint that electrically connects the printed circuit board with the one or more integrated electronic circuit traces of the molded interconnect device.

6. The device of claim 4, wherein the adhesive is applied between the Hall sensor and the printed circuit board and/or between a surface of the device and the printed circuit board.

7. The device of claim 1, wherein the molded interconnect device is configured to be attached on the printed circuit board between pole pieces of a stator of the pump.

8. The device of claim 7, wherein the Hall sensor is configured to output a voltage that is directly proportional to a strength of a magnetic field that is located in a proximity of the pole pieces and the rotor of the pump.

9. An implantable blood pump comprising:
   a housing defining an inlet opening and an outlet opening;
   a dividing wall within the housing defining a blood flow conduit, the blood flow conduit extending between the inlet opening and the outlet opening of the housing;
   a rotary motor including a stator and a rotor, the stator being disposed within the housing circumferentially about the dividing wall such that the blood flow conduit extends through the stator, the stator being disposed circumferentially about at least a part of the rotor and being positioned relative to the rotor such that in use blood flows within the blood flow conduit through the stator before reaching the rotor, and the rotor having permanent magnetic poles for magnetic levitation of the rotor; and
   a molded interconnect device carrying a Hall sensor, the Hall sensor being configured to transduce a position of the rotor, wherein the molded interconnect device comprises one or more integrated electronic circuit traces that are configured to electrically connect the Hall sensor with a printed circuit board of the rotary motor, and wherein the molded interconnect device is mounted to the printed circuit board.

10. The implantable blood pump of claim 9, wherein the molded interconnect device is mounted to the printed circuit board between pole pieces of the stator.

11. The implantable blood pump of claim 10, wherein the stator includes a first coil for driving the rotor and a second coil for adjusting a radial position of the rotor, the first coil and the second coil being wound around one or more of the pole pieces of the stator.

12. The implantable blood pump of claim 9, further comprising:
   at least one recess on a surface of the molded interconnect device, the surface being oriented towards the printed circuit board or facing the printed circuit board.

13. The implantable blood pump of claim 12, wherein the recess is configured to be at least partially filled with an adhesive, and wherein the adhesive is adapted to mount the molded interconnect device to the printed circuit board during operation of the pump after being applied between the Hall sensor and the printed circuit board and/or after being applied between the surface of the molded interconnect device and the printed circuit board.

14. The implantable blood pump of claim 12, wherein the recess is adapted to be form-fit with a soldered joint that electrically connects the printed circuit board with the one or more integrated electronic circuit traces of the molded interconnect device.

15. The implantable blood pump of claim 10, wherein the Hall sensor is configured to output a voltage that is directly proportional to a strength of a magnetic field that is located in a proximity of the pole pieces and the rotor of the pump.

16. The implantable blood pump of claim 9, further comprising:
an active electromagnetic control system configured to radially center the rotor within the blood flow conduit if the position transduced by the Hall sensor is outside a predefined volume within the blood flow conduit.

17. A method of assembling a blood pump, the method comprising:
assembling a motor stator and control electronics in a housing circumferentially about an internal dividing wall, the internal dividing wall defining the a blood flow conduit that extends from an inlet opening to an outlet opening of the housing, the stator being assembled in the housing such that the blood flow conduit extends through the motor stator;
disposing a magnetically-levitated rotor within the blood flow conduit and surrounded by the stator such that impeller blades carried by the rotor are downstream of the rotor from the inlet opening, and such that, in use, the impeller pumps blood from the inlet opening to the outlet opening through the stator;
mounting a molded interconnect device between pole pieces of the motor stator onto a printed circuit board of the motor stator, wherein the molded interconnect device carries a Hall sensor that is configured to transduce a position of the rotor, and wherein the molded interconnect device comprises one or more integrated electronic circuit traces; and
electrically connecting the Hall sensor with the printed circuit board using the one or more integrated electronic circuit traces and electrically connecting the printed circuit board with the control electronics.

18. The method of claim 17, wherein the molded interconnect device is being placed on the printed circuit board by an insertion machine.

* * * * *